United States Patent
Patel et al.

(10) Patent No.: US 7,799,965 B2
(45) Date of Patent: Sep. 21, 2010

(54) WOUND DRESSINGS WITH ANTI-MICROBIAL AND ZINC-CONTAINING AGENTS

(75) Inventors: Harish A. Patel, Norfolk, MA (US); Hansen P. Swaniker, Bristol, RI (US); David G. Heagle, Franklin, MA (US); Kate Ward, Marshfield, MA (US); Alain Tranchemontagne, Warwick, RI (US); E. David Fink, Franklin, MA (US); Ronald F. Vitaris, Worcester, MA (US); Chirag B. Shah, North Attleboro, MA (US); Sharon A. Mulligan, Bristol, RI (US); Brian Dowd, Dedham, MA (US); Scott Orr, Franklin, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 37 days.

(21) Appl. No.: 11/783,668

(22) Filed: Apr. 11, 2007

(65) Prior Publication Data

US 2007/0255193 A1 Nov. 1, 2007

Related U.S. Application Data

(60) Provisional application No. 60/790,814, filed on Apr. 11, 2006.

(51) Int. Cl.
*A61F 13/00* (2006.01)
*A61L 15/16* (2006.01)

(52) U.S. Cl. .......................... 602/48; 602/43; 604/304; 424/443; 424/446; 424/447

(58) Field of Classification Search ................ 602/48, 602/54, 43, 44, 45, 55; 604/310, 312, 383, 604/368, 378, 304, 358, 367; 424/443–449
See application file for complete search history.

(56) References Cited

U.S. PATENT DOCUMENTS

| | | | |
|---|---|---|---|
| 3,431,907 A | 3/1969 | Lubet-Moncla | |
| 4,211,227 A * | 7/1980 | Anderson et al. | ........... 604/366 |
| 5,238,685 A | 8/1993 | Wren | |
| 5,708,023 A | 1/1998 | Modak et al. | |
| 5,763,412 A | 6/1998 | Khan et al. | |
| 5,786,421 A | 7/1998 | Rhee et al. | |
| 5,817,325 A | 10/1998 | Sawan et al. | |
| 5,931,800 A | 8/1999 | Rasmussen et al. | |
| 5,973,221 A | 10/1999 | Collyer et al. | |
| 5,986,164 A | 11/1999 | Kershaw et al. | |
| 6,060,079 A | 5/2000 | Freeman et al. | |
| 6,369,289 B1 * | 4/2002 | Orr, III | ........... 602/48 |
| 6,730,329 B1 | 5/2004 | Smith | |
| 6,762,339 B1 * | 7/2004 | Klun et al. | ........... 602/58 |

(Continued)

FOREIGN PATENT DOCUMENTS

CN 1170564 A 1/1998

(Continued)

*Primary Examiner*—Patricia M Bianco
*Assistant Examiner*—Ophelia Hawthorne
(74) *Attorney, Agent, or Firm*—Elizabeth A. O'Brien, Esq.

(57) ABSTRACT

A wound dressing includes one or more layers containing a first anti-microbial agent and/or at least one zinc-containing agent.

28 Claims, 1 Drawing Sheet

U.S. PATENT DOCUMENTS

| | | |
|---|---|---|
| 6,861,570 B1 | 3/2005 | Flick |
| 7,005,556 B1 | 2/2006 | Becker et al. |
| 7,270,721 B2 * | 9/2007 | Hilfenhaus et al. ............ 156/60 |
| 2003/0176827 A1 * | 9/2003 | Chandra et al. ............... 602/48 |
| 2004/0015115 A1 | 1/2004 | Sinyagin |
| 2004/0047763 A1 | 3/2004 | Kite et al. |
| 2004/0076662 A1 | 4/2004 | Riesinger |
| 2004/0082925 A1 * | 4/2004 | Patel ......................... 604/289 |
| 2004/0180093 A1 | 9/2004 | Burton et al. |
| 2004/0241216 A1 | 12/2004 | Klun et al. |
| 2004/0243041 A1 * | 12/2004 | Qin et al. ...................... 602/41 |
| 2004/0258914 A1 | 12/2004 | Chandra et al. |
| 2005/0124724 A1 | 6/2005 | Burton et al. |
| 2006/0018966 A1 | 1/2006 | Lin et al. |
| 2006/0051385 A1 | 3/2006 | Scholz |
| 2007/0020315 A1 * | 1/2007 | Shannon et al. ............. 424/443 |

FOREIGN PATENT DOCUMENTS

| | | |
|---|---|---|
| CN | 1537640 A | 10/2004 |
| WO | WO 02/38097 A1 * | 5/2002 |

* cited by examiner

WOUND DRESSINGS WITH ANTI-MICROBIAL AND ZINC-CONTAINING AGENTS

The present nonprovisional application claims priority, pursuant to 35 U.S.C. §119, to provisional application Ser. No. 60/790,814 filed Apr. 11, 2006, the entire content of which is incorporated herein by reference.

BACKGROUND

In the discussion of the state of the art that follows, reference is made to certain structures and/or methods. However, the following references should not be construed as an admission that these structures and/or methods constitute prior art. Applicant expressly reserves the right to demonstrate that such structures and/or methods do not qualify as prior art.

A variety of wound dressings have been suggested. However, such wound dressings possess various deficiencies and shortcomings.

For example, a number of wound dressings have been proposed which include various anti-microbial agents. Logically, an increase in the amount of anti-microbial agent contained in the wound dressing would suggest an increase effectiveness in combating and/or preventing infection. However, certain popular anti-microbial agents, such as chlorohexidine gluconate (CHG) can have an irritating effect on the skin, especially when higher levels or concentrations of CHG are applied.

Thus, a need exists in the art for wound dressings which have a relatively greater effectiveness in combating and/or preventing infection, but which do not possess disadvantages, such as increased skin irritation.

SUMMARY

According to one optional aspect of the present invention, improved control of bioburden is provided, without resorting to increased concentrations of anti-microbial agents, such as PHMB. According to a further optional aspect of the present invention, the wound dressing is provided which reduces the risk of infection, or facilitates the control of an existing infection, without change to the existing wound care protocol. According to yet a further optional aspect of the present invention, there is provided a wound dressing which will effectively increase the spectrum of activity of the anti-microbial agent contained therein. According to another optional aspect of the present invention, a wound dressing is provided which provides targeted and/or controlled delivery of an anti-microbial agent and/or additional additives contained in the wound dressing to the wound site.

According to one aspect of the present invention, there is provided a wound dressing comprising one or more layers containing at least one anti-microbial agent and/or at least one zinc-containing agent.

A wound dressing according to an alternative embodiment of the present invention comprises at least a first layer, a second layer and a third layer, wherein at least one of the first, second and third layers contains an anti-microbial agent and/or a zinc-containing the agent.

According to another aspect of the present invention, there is provided a wound dressing comprising at least a first layer, a second layer and a third layer, wherein at least the one of the first, second and third layers contains an anti-microbial agent, and at least another of the first, second and third layers contains a zinc-containing agent.

A wound dressing formed according to a further embodiment comprises a first inner layer containing an anti-microbial agent; and second and third outer layers adjacent to the first layer, the second and third layers containing a zinc-containing agent.

According to yet another aspect of the present invention, there is provided a wound dressing comprising: a first inner layer; and second and third outer layers, wherein each of the first, second and third layers contain an anti-microbial agent and a zinc-containing agent.

A wound dressing formed according to a further alternative embodiment comprises one or more layers formed from a combination of fibers, the combination of fibers comprising at least a first fiber and a second fiber, wherein the first fiber is treated with at least a first anti-microbial agent, and the second fiber is treated with at least a second agent.

According to an additional alternative aspect of the present invention, there is provided a wound dressing comprising one or more layers formed from a homogenous blend of fibers, the combination of fibers comprising at least a first fiber and a second fiber, wherein the first fiber is treated with at least a first anti-microbial agent, and a second fibers treated with at least a second agent.

A wound dressing formed according to a further alternative embodiment comprises one or more layers formed from a combination of fibers, the combination of fibers comprising at least a first fiber and a second fiber, wherein the first fiber is treated with at least a first anti-microbial agent, and the second fiber is treated with at least a second agent, and wherein the amount of first fiber present in the wound dressing is different than the amount of second fiber present in the wound dressing.

According to still another embodiment of the present invention, a wound dressing comprises one or more layers formed from a combination of fibers, the combination of fibers comprising at least a first fiber and a second fiber, wherein the first fiber is treated with at least a first anti-microbial agent, and the second fiber is treated with at least a second agent, and wherein the density of either the first fiber, second fiber, or both, vary along a concentration gradient.

A wound dressing formed according to an additional alternative embodiment comprises a first layer disposed on a first side of the dressing adapted to be applied to the wound surface, the first layer containing at least one anti-microbial agent and a zinc-containing agent; and a second layer adjacent to the first layer, and disposed on a side thereof opposite the first side of the dressing.

As used herein "containing" or "contains" is broadly construed to mean that the one or more layers themselves and/or the material(s) making up the layers are impregnated with, and/or have a surface applied coatings/treatments of another material(s)/agent(s). The impregnation and/or surface coatings/treatments may be applied to all or a portion of the layers or the material(s) forming the layers. Finally, the term encompasses all methods or techniques of impregnation and/or surface coatings/treatments, regardless of the state of the material(s)/agent(s) being applied thereto (e.g., solid, liquid, gas, plasma, etc.). The added material(s)/agent(s) can be applied during manufacture, or subsequent thereto (e.g., by the user/consumer prior to application of the one or more layers to the wound site).

DETAILED DESCRIPTION

Figure 1:
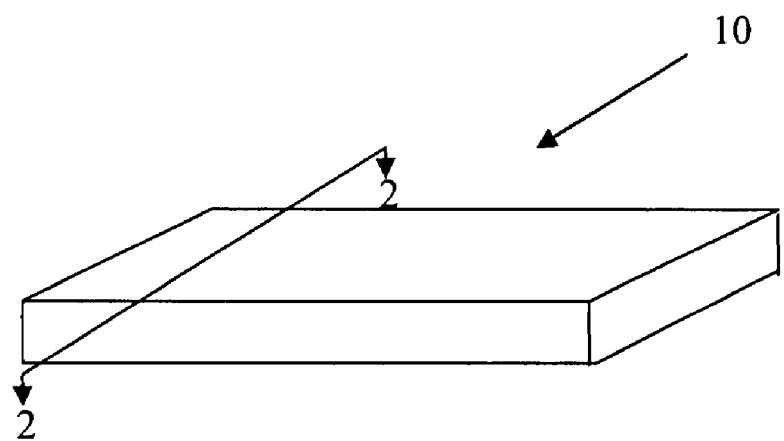
FIG. 1 is a schematic illustration of an exemplary embodiment of an anti-microbial wound dressing of the present invention.
Figure 2:
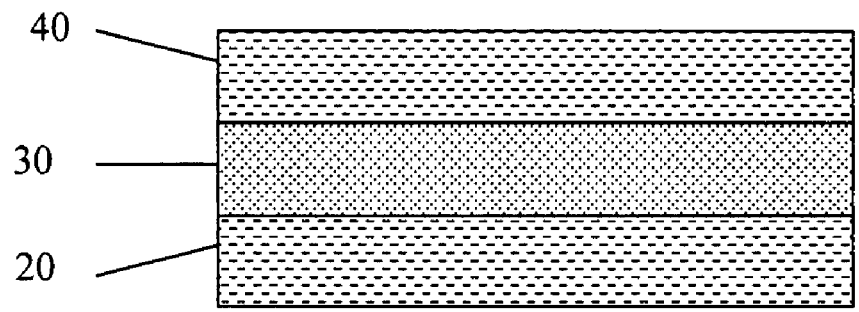
FIG. 2 is a schematic cross-sectional illustration, taken along lines 2-2 of FIG. 1 of alternative embodiments of an anti-microbial wound dressing of the present invention.

FIGS. 1-2 may be referred to in order to facilitate the following discussion. In broader aspects, the present invention provides a wound dressing (10) comprising one or more layers containing a first anti-microbial agent and at least one zinc-containing agent.

A wound dressing formed according to the principles of the present invention can be generally formed from one or more discrete layers (e.g., 20, 30, 40). Each of the one or more layers can be formed from any suitable material and/or construction. For example, the one or more layers can be formed from a fibrous, film-like, foam and/or gel material. With respect to fibrous materials, they can be woven or nonwoven materials. The fibers can be selected from natural fibers, synthetic fibers, and combinations of the two. By way of non-limiting example, suitable materials which can be utilized to form the one or more layers of the present invention include: cellulose, alginates (e.g., calcium alginate), cotton, Rayon, Nylon, acrylic, polyester, polyurethane, polyurethane foam, a hydrogel and combinations thereof.

A wound dressing of the present invention may include one or more anti-microbial agents. A number of alternative anti-microbial agents are possible. Suitable anti-microbial agents include, but are not limited to, a chlorhexidine, a chlorhexadine salt, a triclosan, a Polymyxin, a tetracycline, an amino glycoside (e.g., gentamicin or Tobramycin™), a rifampicin, a bacitracin, an erythromycin, a neomycin, a chloramphenicol, a miconazole, a quinolone, a penicillin, a nonoxynol 9, a fusidic acid, a cephalosporin, a mupirocin, a metronidazole, a secropin, a protegrin, a bacteriolcin, a defensin, a nitrofurazone, a mafenide, aracyclovir, a vanocmycin, a clindamycin, a lincomycin, a sulfonamide, a norfloxacin, a pefloxacin, a nalidizic acid, an oxalic acid, an enoxacin acid, a ciprofloxacin, a biguanide, combinations thereof and the like. In certain embodiments the anti-microbial agent comprises polyhexamethylene biguanide (PHMB) and/or derivatives thereof.

A wound dressing of the present invention may further include a zinc containing agent. Any suitable zinc-containing agent may be utilized. By way of non-limiting example, zinc-containing agents such as a zinc aliginate or a zinc aspartate, combinations thereof and the like, are contemplated. Zinc-containing agents can improve the rate of wound healing, thereby rendering the wound dressing more effective in combating and/or preventing infection, without the necessity of increasing the levels of anti-microbial agent contained therein. Combination with an aliginate provides moisture-absorption capabilities, and alginates help promote a moist wound healing environment. This aspect of the present invention advantageously avoids problems caused by the irritating effects of certain anti-microbial agents, such as CHG, especially when applied to the skin in higher concentration levels.

As an additional component, or as a substitute for one or more of the above-mentioned anti-microbial agents and/or zinc-containing agents, a wound dressing formed according to the principles of the present invention may include one or more additional anti-microbial agents. By way of non-limiting example, suitable additional anti-microbial agents include, but are not limited to: polyethylene hexamethylene biguanide (PEHMB), ionic metals, silver, zinc, copper and combinations thereof.

Exemplary wound dressings can, of course, include additional active ingredients or agents such as, for example, a therapeutic agent, an organoleptic agent, a growth factor, an analgesic, a tissue scaffolding agent, a haemostatic agent, a protein inhibitor, collagen, enzymes, an anti-thrombogenic agent, an anesthetic, an analgesic, an anti-inflammatory agent, an anticancer agent, a vasodilation substance, nitric oxide, petroleum jelly, vitamins, taurine, capsaicin, menthol, a wound healing agent, an angiogenic agent, an angiostatic agent, an immune boosting agent, a skin sealing agent, an agent to induce directional bacterial growth, an agent to impart bacteriacidal or bacteriostatic activity, an electron transfer agent to destabilize or destroy the metabolic action of microbes and/or biofilm formation, combinations thereof and the like. Release of active agents may be triggered by a variety of means, such as, for example, electric field or signal, temperature, time, pressure, moisture and light including, for example, ultra-violet light, ultrasound energy, sonication, combinations thereof and the like.

According to the present invention, any of the above-mentioned anti-microbial, zinc-containing, or additional active agents may be combined directly with the material forming the one or more layers of the wound dressing. Alternatively, any of the above-mentioned agents may be contained, and subsequently released, by a delivery agent. Any suitable delivery agent can be utilized. By way of non-limiting example, suitable delivery agents include: a hydrogel, powdered starch, dissolvable phosphate glass or a starch film.

The anti-microbial, zinc-containing agent, and/or or other agent mentioned above can optionally be printed or otherwise applied to one or more layers of a wound dressing to provide a desired concentration or concentration gradient of one or more of these agents on and/or within the dressing. For example, one or more of the agents can be applied separately, or in combination, in a specific pattern corresponding to the wound area, for the purpose of optimizing the anti-mircobial and wound healing effects. Alternatively, the anti-microbial and/or zinc-containing agent can be uniformly and homogenously combined with the material forming one or more layers of the wound dressing.

Wound dressings formed according to the present invention can be provided in numerous configurations, having a number of different combinations of features. In the discussion that follows, any of the above-mentioned agents or additives can be included in the illustrative configurations discussed below, unless otherwise indicated.

According to one possible configuration of the present invention, a wound dressing is provided which comprises one or more layers containing at least one anti-microbial agent and at least one zinc-containing agent. According to one optional modification, all layers of the wound dressing may contain a combination of anti-microbial agent and zinc-containing agent.

According to another alternative modification of the above configuration, the wound dressing comprises a plurality of layers and the anti-microbial agent and the zinc-containing agent can be separately contained in different layers of the wound dressing. As one possible modification of this configuration, at least one of the layers contains both an anti-microbial agent and a zinc-containing agent. For example, a wound dressing can be formed with at least three distinct layers; a first inner layer (e.g., 30), and adjacent outer layers (e.g., 20, 40). According to one specific non-limiting example, the individual layers can be formed from cotton, foam and a film, and can be provided in any order of arrangement. The anti-microbial agent can be contained in the first inner layer, which is not in direct contact with the skin or wound, and the zinc-containing agent can be provided in one or more of the outer layers. The inner layer may be substantially hydrophilic, while one or more of the outer layers may be substantially hydrophobic. Optionally, one or more outer layers are provided with a hydrophilic finish. Although an anti-microbial agent, and possibly also a zinc-containing agent, may be released from the inner layer material of the fabric, the anti-microbial treatment of the fabric principally allows the dressing to function as a barrier to contamination of the wound from sources outside the wound. In addition, due to the absorbent characteristics of the dressing, microbes absorbed within the inner layer are prevented from escaping through the dressing. The term "substantially hydrophilic" describes the function of the inner layer material. It also distinguishes the inner layer material over the function of the "substantially hydrophobic" outer layer material, which provides an anti-microbial barrier property and attenuates or reduces the release of anti-microbial agent away from the dressing. The improved retention of anti-microbial agent within the inner layer also lowers the bioburden, i.e., the growth and number of cells, within the dressing during use. As an optional modification of the above, the zinc-containing agent can be provided in the inner layer, and the anti-microbial agent provided in one or more of the adjacent outer layers.

When the wound dressings of the present invention are formed from fibrous materials, the wound dressing can be provided with a combination of anti-microbial agents and/or zinc-containing agents by treating different fibers with different agents, then combining the fibers in a desired manner to provide the wound dressing with a particular anti-microbial effect or behavior. Thus, for example, the wound dressing may comprise one or more layers formed as a homogenous blend of the above described treated fibers. Alternatively, the wound dressing can be formed from one or more layers composed of fibers which vary in density and anti-microbial treatment levels. By way of nonlimiting example, suitable fibers such as cellulose, Rayon, etc. can be treated and bound to PHMB in various concentrations. Other fibers, such as nylon or polyester, can be compounded with a zinc-containing agent in the base resin, and spun into fiber form. As an alternative, the fiber can be constructed from two basic components. Specifically, the fiber can comprise an inner core and an outer sheath which contains a relatively higher amount of anti-microbial and/or zinc-containing agent. It is contemplated that other combinations of anti-microbial agents are possible. By way of non-limiting example, other metal-based anti-microbial agents, such as those based on silver or copper, could be utilized in combination with or instead of the zinc-containing agent.

According to one alternative embodiment of the present invention, a wound dressing can be provided that comprises a plurality of layers. One layer, for example, the wound contact layer is formed from a calcium aliginate material and contains a combination of anti-microbial agent (e.g., PHMB) as well as a zinc-containing agent. An additional layer, or top player, is disposed above the wound contact layer and is made from a different wound dressing material (e.g., woven or nonwoven fabric, phone, gel or film). This top layer may optionally include an anti-microbial agent as well.

All numbers expressing quantities of ingredients, constituents, reaction conditions, and so forth used in the specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, may inherently contains certain errors as evident from the standard deviation found in their respective measurement techniques.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

We claim:

1. A wound dressing comprising a first layer, second layer and third layer wherein each of the first, second and third layers contain at least one anti-microbial agent and at least one zinc-containing agent.

2. The wound dressing of claim 1, wherein the first layer is substantially hydrophilic, and the second and third layers are outer layers and are substantially hydrophobic.

3. The wound dressing of claim 2, wherein the second and third outer layers comprise a hydrophilic finish.

4. The wound dressing of claim 1, wherein the anti-microbial agent comprises one or more of: PHMB, PHMB derivatives, PEHMB, silver, copper and combinations thereof.

5. The wound dressing of claim 4, wherein a zinc-containing agent comprises one or more of zinc alginate and zinc aspartate.

6. The wound dressing of claim 1, further comprising a delivery agent for containing and releasing at least one of the agents.

7. The wound dressing of claim 6, wherein the delivery agent comprises one or more of: a hydrogel, powdered starch, a dissolvable phosphate glass or a starch film.

8. The wound dressing of claim 1, wherein one or more layers are formed, at least in part, by one or more of: natural fibers, synthetic fibers, cellulose, cotton, Rayon, Nylon, acrylic, polyester, polyurethane, polyurethane foam, a hydrogel, a starch film, calcium alginate an absorbable material and combinations thereof.

9. The wound dressing of claim 1, further comprising one or more of: a therapeutic agent, an organoleptic agent, a growth factor, an analgesic, a tissue scaffolding agent, a haemostatic agent, a protein inhibitor, collagen, enzymes, an anti-thrombogenic agent, an anesthetic, an analgesic, an anti-inflammatory agent, an anticancer agent, a vasodilation substance, nitric oxide, petroleum jelly, vitamins, taurine, capsaicin, menthol, a wound healing agent, an angiogenic agent, an angiostatic agent, an immune boosting agent, a skin sealing agent, an agent to induce directional bacterial growth, an agent to impart bacteriocidal or bacteriostatic activity, an electron transfer agent to destabilize or destroy the metabolic action of microbes and/or biofilm formation, and combinations thereof.

10. The wound dressing of claim 1, further comprising an adhesive.

11. The wound dressing of claim 1, further comprising at least one of the anti-microbial agent and the zinc-containing agent disposed in a pattern on at least one of the layers.

12. The wound dressing of claim 1, wherein at least one layer is formed from calcium alginate and contains a zinc-containing agent and PHMB.

13. The wound dressing of claim 1, wherein at least one layer is formed from cotton fiber, at least one layer is formed from a foam, and at least one layer is formed from a film.

14. The wound dressing of claim 1, wherein the at least once zinc containing agent comprises zinc aspartate.

15. The wound dressing of claim 1, wherein at least one of the first, second or third layers is a skin-contacting layer.

16. A wound dressing comprising a first layer and a second layer, wherein the first layer is disposed on a first side of the dressing adapted to be applied to the wound surface, the first layer containing the at least one anti-microbial agent; and the second layer is adjacent to the first layer, and disposed on a side thereof opposite the first side of the dressing, the second layer containing the at least one zinc-containing agent, wherein the anti-microbial agent comprises one or more of: PHMB, PHMB derivatives, and PEHMB.

17. The wound dressing of claim 16, further comprising a third layer, wherein the first layer is substantially hydrophilic, and the second and third layers are outer layers and are substantially hydrophobic.

18. The wound dressing of claim 17, wherein the second and third outer layers comprise a hydrophilic finish.

19. The wound dressing of claim 16, wherein the anti-microbial agent further comprises silver, copper and combinations thereof.

20. The wound dressing of claim 19, wherein a zinc-containing agent comprises one or more of zinc alginate and zinc aspartate.

21. The wound dressing of claim 16, further comprising a delivery agent for containing and releasing at least one of the agents.

22. The wound dressing of claim 21, wherein the delivery agent comprises one or more of: a hydrogel, powdered starch, a dissolvable phosphate glass or a starch film.

23. The wound dressing of claim 16, wherein one or more layers are formed, at least in part, by one or more of: natural fibers, synthetic fibers, cellulose, cotton, Rayon, Nylon, acrylic, polyester, polyurethane, polyurethane foam, a hydrogel, a starch film, calcium alginate an absorbable material and combinations thereof.

24. The wound dressing of claim 16, further comprising one or more of: a therapeutic agent, an organoleptic agent, a growth factor, an analgesic, a tissue scaffolding agent, a haemostatic agent, a protein inhibitor, collagen, enzymes, an anti-thrombogenic agent, an anesthetic, an analgesic, an anti-inflammatory agent, an anticancer agent, a vasodilation substance, nitric oxide, petroleum jelly, vitamins, taurine, capsaicin, menthol, a wound healing agent, an angiogenic agent, an angiostatic agent, an immune boosting agent, a skin sealing agent, an agent to induce directional bacterial growth, an agent to impart bacteriocidal or bacteriostatic activity, an electron transfer agent to destabilize or destroy the metabolic action of microbes and/or biofilm formation, and combinations thereof.

25. A wound dressing comprising at least one layer, wherein one or more layers comprise a combination of fibers, the combination of fibers comprising at least a first fiber and a second fiber, wherein the first fiber comprises at least a first anti-microbial agent, and the second fiber comprises at least a zinc-containing agent.

26. The wound dressing of claim 25, wherein one or more layers comprise a homogenous blend of fibers.

27. The wound dressing of claim 25, wherein the amount of first fiber present in the wound dressing is different than the amount of second fiber present in the wound dressing.

28. The wound dressing of claim 25, wherein the density of either the first fiber, second fiber, or both, vary along a concentration gradient.

* * * * *